United States Patent [19]

Ghebre-Sellassie et al.

[11] Patent Number: 4,814,354
[45] Date of Patent: Mar. 21, 1989

[54] LIPID REGULATING AGENTS

[75] Inventors: Isaac Ghebre-Sellassie, Stanhope; Robert H. Gordon, Dover; Mahdi B. Fawzi, Flanders, all of N.J.

[73] Assignee: Warner-Lambert Company, Morris Plains, N.J.

[21] Appl. No.: 912,903

[22] Filed: Sep. 26, 1986

[51] Int. Cl.$^4$ .......................... A61K 9/68; A61K 9/28; A61K 31/74

[52] U.S. Cl. ...................................... 424/440; 424/48; 424/79

[58] Field of Search ............................ 424/48, 79, 440

[56] References Cited

U.S. PATENT DOCUMENTS

| 4,716,033 | 12/1987 | Denick | 424/441 |
| 4,747,881 | 5/1988 | Shaw et al. | 514/951 |
| 4,753,800 | 6/1988 | Mozda | 424/440 |

FOREIGN PATENT DOCUMENTS

| 0040590 | 11/1981 | European Pat. Off. . |
| 227603 | 7/1987 | European Pat. Off. . |

OTHER PUBLICATIONS

Yang et al., C.A.108:26960m (1988) of EPO227603, Jul. 1, 1987.

*Primary Examiner*—Shep K. Rose
*Attorney, Agent, or Firm*—Ronald A. Daignault

[57] ABSTRACT

Cholestyramine can be administered orally along with one or more other lipid regulating agent(s) and/or other beneficial agent(s) in compositions in which the cholestyramine has been suitably pretreated.

6 Claims, No Drawings

LIPID REGULATING AGENTS

BACKGROUND

Cholestyramine is a well-known ion-exchange resin which has pharmaceutical utility as a non-systemic agent which lowers serum cholesterol. During normal digestion, most of the bile acids secreted into the duodenum are recaptured at specific ileal receptor sites and returned to the liver via the enterohepatic circulation. Cholestyramine resin combines with the bile acids to form an insoluble complex that is excreted in the feces, thereby leading, eventually, to a decrease in serum cholesterol levels.

While cholestyramine is effective as an antihyperlipemic, it is gritty or sandy in texture making it unpleasant in appearance and mouthfeel. One result of this unpleasantness is reduced patient compliance. That is, individuals who ingest the resin regularly may avoid taking all of the resin they need on a daily basis.

Combination products, i.e., compositions which contain cholestyramine and one or more other lipid regulators, are difficult to formulate because of the ionic character of the resin. Thus an acidic nonionic lipid lowering agent, such as gemfibrozil, cannot be readily administered along with cholestyramine because the acidic agent can bind to the ionic sites on the resin, and thereby reduce the effectiveness of both agents.

THE INVENTION

It has been discovered that useful compositions containing one or more lipid regulators along with cholestyramine or other lipid modifiers of non-systemic character can be produced by pretreating the ionic lipid modifier using a certain regimen and combining that pretreated material with at least one other lipid lowering agent.

In one embodiment, cholestyramine resin is granulated to yield granules whose particle size ranges from about 10 to about 100 microns. These granules are then coated with a material which is acid resistant, but soluble in the intestinal juice which is present in that portion of the intestines where bile acids are secreted. This pretreated cholestyramine can then be administered alone or in combination with other lipid modifying agent(s).

ADVANTAGES

The compositions of the invention have several advantages over known compositions containing cholestyramine resin. Patient compliance will be increased because compositions containing combinations of two or more lipid regulators need not be administered as often. For instance, different dosage forms can be administered concurrently. In addition, the pretreated cholestyramine resin is in a form which makes it readily includable into various dosage forms such as candy bars, chewing gums, liquid and semi-solid suspensions, sprinkle systems, tablets capsules and the like.

Furthermore, the coating process used in the pretreatment virtually assures that the cholestyramine or other ionic component will not react to any significant extent before it reaches the proper location in the gastrointestinal tract so that its efficacy is maximized.

These and other aspects and advantages of the invention will be readily apparent upon consideration of the following description of the invention.

DESCRIPTION OF THE INVENTION

The invention involves a composition and a method by which the interaction between cholestyramine and other drugs, especially other lipid regulating drugs, is minimized when ingested in combination by human subjects.

The compositions of the invention contain:

(a) at least one primary lipid regulator which has been pretreated to render it stable until it reaches the proximal section of the intestines, and (b) at least one other therapeutically active substance which acts in cooperation with the ingredient(s) in (a) to regulate lipids in the bloodstream or otherwise improve a patients' health after the composition is ingested in combination orally.

The process of the invention involves the administration of a drug combination to a patient in need of hyperlipidemic therapy. In general, the process involves the use of one composition in a series of compositions which are formulated such that the active or reactive agents in each drug is absorbed with maximum efficiency in the body.

It is preferred that the cholestyramine or other lipid regulator of ionic character be pretreated via a process which involves:

(1) granulation; and
(2) coating with an acid resistant coating material.

It is highly preferred that the coating material used in step (2) be soluble in the juices of the proximal region of the intestine, i.e., in that portion of the intestine in which bile acids are present in significant amounts. By "significant amounts" applicants mean quantities in which bile acids can be effectively bound to the reactive sites of an ionic lipid modifier such as cholestyramine.

Lipid Reoulators

The drug combinations of the invention will combine a primary lipid regulator, e.g., cholestyramine and at least one secondary lipid regulator.

The primary lipid regulators useful in the invention can be selected from any of the ionic types conventionally employed to bind bile salts and/or other fatty materials. By "ionic" applicants mean that the substance is ionizable throughout the pH gradient of gastrointestinal tract. Useful primary lipid regulators include those which act by ionic mechanisms indirectly to remove one or more fatty substances from the bloodstream and to receive the concentration of some in fecal excretions.

Preferred lipid modifiers of the ionic type are cholestyramine, colestipol, and the like and their pharmaceutically acceptable salts, e.g., cholestipol HCl. Cholestyramine and other anionic exchange resins, are contemplated.

Cholestyramine is a pharmacologically important anionic-exchange resin. The basic quaternary ammonium-exchange functionalities in the resin are attached to a styrene divinylbenzene copolymer skeleton.

Its structure is:

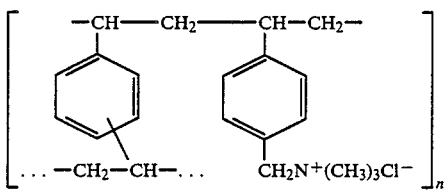

wherein n is a function of molecular weight.

It has been demonstrated in animals and clinically in man that cholestyramine is capable of increasing the fecal excretion of endogenous bile salts, thereby significantly decreasing the extent of absorption of fats and fatty materials. This resin also possesses the ability to lower plasma cholesterol levels by binding bile-salt anions in the small intestine. One article which discusses the resins binding capacity is W. J. Johns and T. R. Bates, "Quantification of the Binding Tendencies of Cholestyramine I; Effect of Structure and Added Electrolytes on the Binding of Unconjugated and Conjugated Bile-Salt Anions," *Journal of Pharm. Science*, vol. 58, No. 2, February, 1969, pp. 179–83. The content of that article is hereby incorporated by reference.

The secondary lipid regulator(s) to be employed in the compositions of the invention can be any of a wide variety of non-ionic lipid or fatty-substance reducers which act by mechanisms other than ionic bonding. By "non-ionic" applicants mean that the lipid modifier is ionizable only at certain pH. For example, COOH groups are ionizable at neutral to alkaline pH.

Applicants contemplate formulations in which cholestyramine and/or other lipid modifiers of ionic character are used in combination with one or more agents which inhibit the production and/or absorption of cholesterol. Suitable agents include, but are not limited to, fibric acid derivatives, cholereductase inhibitors, antihyperlipoproteinemics and the like.

Useful lipid lowering/regulating agents include—but are not limited to—gemfibrozil, dextrothyroxine, the fibrates, eg., fenofibrate, clofibrate, bezafibrate, ciprofibrate, mevinolin, synvinolin, niacin, hormonal preparations, eg., T3- and/or T4- containing agents, fish oils and/or extracts of such oils, eptastin, the neomycins, probucol, nicotinic acid, and the like, as well as their pharmaceutically acceptable salts and esters, eg., dextrothyroxine sodium, gemfibrozil HCl and the like. Gemfibrozil and its pharmaceutically acceptable derivatives are preferred.

Gemfibrozil and its analogs are discussed in U.S. Pat. Nos. 3,674,836 and 4,126,637, the disclosures of which are hereby incorporated by reference.

Mixtures of lipid moderators which are not of ionic character are operable, as are mixtures which contain a plurality of ionic-type moderators and a plurality of one or more other types.

The quantities in which each of the lipid reducing agents will be present in the final therapeutic compositions will vary depending upon the nature of the agents selected and the desired therapeutic effect to be achieved.

In general, in compositions containing cholestyramine, the concentration of cholestyramine will be from about 5 to about 80, preferably about 30 to about 60 weight percent, based on total composition weight. If another lipid modifier of ionic character is used, its concentration will be from about 30 to about 60 wt. percent.

Unless stated otherwise all percentages stated herein are weight percentages, based on total composition weight.

When a secondary lipid modifier is used—i.e., one which is not of ionic character—it will generally be present in a concentration of about 5 to about 80, preferably about 30 to about 60, weight percent by weight.

If desired, part or all of the secondary lipid reducing agent can be replaced by a beneficial substance other than a lipid regulator. Thus, one or more vitamins, minerals, analgesics, alkaloids, antihistamines, decongestants, muscle relaxants, and the like can be used in the combinations of the invention.

PRETREATMENT TECHNIQUE

The process by which the primary ionic lipid reducer is treated in order to maximize its compatability with other drugs in the system is a novel one.

In a preferred embodiment cholestyramine is granulated and coated to render it more efficacious when taken in combination with gemfibrozil.

The granulation step involves agglomeration or other suitable processing to yield granules or other generally spherical particles whose size range from about 30 to about 100, microns.

Following granulation, the particles are then coated with a pharmaceutically acceptable material which is acid resistant, so that the granules remain coated as they pass through the stomach after ingestion.

It is highly preferred that the acid resistant coating also be soluble in that region of the intestines in which bile salts and other fatty substances can be absorbed, or bound, by the resin, so that they are taken out before they reach the bloodstream and excreted along with fecal matter. Suitable coating materials are commercially available materials, or combinations of some, which have the requisite solubility.

In general, the coating material should be insoluble at pH's less than 5, preferably pH's less than 4, but soluble at the pH of the proximal intestine, i.e., about 4 to about 7, preferably about 4 to about 5.

Preferred coating materials are polymers or polymer precursors whose films ave the solubility properties discussed above. Useful coating systems include cellulose acetate phthalate, polyvinylacetate phthalate, Eudragit L-100 and the like. Mixtures are operable.

The method by which the coating material(s) is applied to the primary lipid regulator is not crucial. It is sufficient for the purposes of this invention that this lipid regulator be coated, encapsulated or otherwise treated with the coating material so that little or no association of the ionic lipid regulator takes place in an acid environment, i.e., in the stomach.

Optionally, the secondary lipid modifier or other drug employed in the combinations of the invention can be suitable pretreated. One preferred treatment involves the taste-masking system set out in U.S. Ser. No. 701,470 W-L PD #3282-7-DAS.

DOSAGE FORMS

The final dosage forms in which the drug combinations of the invention will be delivered can vary broadly. Since the compositions are to be administered orally, it is contemplated that any system which affords ingestion via the gastro-intestinal tract can be used. Thus formulations which result in tablets, pellets, sprinkles, suspensions, gels, candy bars, chewy candy, chewing gums, lozenges, and the like are contemplated. Combinations of these, e.g., lozenges with chewing candy centers are useful.

One preferred dosage form is an edible candy formulation. Suitable candy formulations contain fillers, waxes, sweeteners, stabilizers, flavoring agents, fragrance enhancers, processing aids, and the like, which are conventionally used in the confectionery arts. For example, suitable sweeteners include aspartame, saccharine, glucose, sucrose, fructose, xylitol, and the like and combinations thereof.

Excipients, such as fillers, stabilizers and other additives conventionally employed in the pharmaceutical industry and in the candy and confectionery industry, can be used in suitable amounts in the compositions of the invention.

The dosage forms produced in accordance with the invention will be employed to deliver drugs to human recipients in suitable quantites for the therapeutic effect(s) desired, ie., at dosage levels which are consistent with the therapeutic needs of the patient and the desires of his or her physician. Thus, daily dosage levels are well-known for the lipid regulators employed in the invention and need not be spelled out here. Typically, reference sources such as the *Physicians' Desk Reference*, and drug manufacturer's specifications and instructions can be consulted to determine proper drug concentration levels and/or dosage regimens for the combinations of the invention.

EXAMPLES

The following examples illustrate the invention.

Example I

This example shows the effect of pH on the binding of gemfibrozil to untreated cholestyramine.

Gemfibrozil solutions were prepared in 0.05M acetate buffer, pH 4.5, and in 0.05M phosphate buffer, pH 6.0 and 7.5 as follows:

Gemfibrozil solutions were prepared by adding an excess of gemfibrozil to the desired volume of buffer and agitating overnight on a shaker at room temperature. The resulting suspension was vacuum filtered. Gemfibrozil concentration was determined from absorbance at 280 nm, using $A_{1cm}^{1\%} = 65.6$ Ultraviolet absorbance measurements were obtained on a Beckman DU-7 spectrophotometer.

Optical rotation measurements at the sodium D line were made with a Rudolph Auto-Pol 2.

All experiments were conducted (unless otherwise noted) in 50 or 15 ml polypropylene centrifuge tubes with plug and caps. The mixtures were always agitated at 75 RPM on a Vanderkamp Sustained Release Apparatus heated to 37° C.

Sodium Glycocholate: Sigma; Lot #75F-5083
Cholestyramine: Rohm & Haas, Amberlite - IRP 276; Lot #6X686

The concentration of gemfibrozil in each buffer, determined from absorbance at 280 nm was: pH 4.5, 0.014 mg/ml; pH 6.0, 0.150 mg/ml; pH 7.5, 1.711 mg/ml. Cholestyramine (10 mg) was added to 20 ml of each gemfibrozil solution and the mixtures were agitated for 2 hours. The mixtures were filtered and the concentration of unbound gemfibrozil was determined.

The solubility of gemfibrozil at pH 4.5 is very low, as shown in Table I. Therefore, despite the fact that gemfibrozil has a high affinity for cholestyramine, very little gemfibrozil is available for binding at this pH. At pH 6.0, paralleling the increase in gemfibrozil solubility (Table I) is an increase in the amount bound. At pH 7.5, the amount of gemfifbrozil in solution is greater than the amount needed to saturate the resin and saturation, indeed, occurs. It is of interest that pH's of 4.5 and 6.0, the resin does not bind 100% of the available gemfibrozil, despite the fact that unoccupied binding sites are present.

TABLE I

Binding of Gemfibrozil to Cholestyramine at Various pH's.

| pH | mmol Gemfibrozil Bound/g Resin |
|---|---|
| 4.5 | 0.11 |
| 6.0 | 0.60 |
| 7.5 | 2.83 |

Example II

This example shows the effect of pH on the binding of gemfibrozil which has been treated in accordance with the invention. The experimental procedure was the same as in Example I. The coated material contained fifty percent active resin.

TABLE II

Binding of Gemfibrozil to Treated Cholestyramine

| pH | mmol Gemfibrozil Bound/g Resin |
|---|---|
| 4.5 | 0.06 |
| 6.0 | 0.66 |
| 7.5 | 2.83 |

Example III

Table III sets forth drug concentrations in compositions which are useful in lowering serum cholesterol levels in human subjects when administered orally. These compositions contain both treated cholestyramine and gemfibrozil in the amounts indicated.

TABLE III

| Cholestyramine/Gemfibrozil Combinations | | |
|---|---|---|
| | Broad Range | Preferred Range |
| Cholestyramine* (grams) | 2–20 | 4–16 |
| Gemfibrozil (milligrams) | 100–2,000 | 300–1,600 |

*weight of untreated cholestyramine resin

Reasonable variations, such as those which would occur to a skilled artisan, can be made herein without departing from the scope of the invention.

We claim:

1. A pharmaceutical composition comprising a chewy candy containing;
   (a) an anion exchange resin lipid regulator or a pharmaceutically acceptable salt thereof in granular form of 30–100 microns with a gritty or sandy texture, and ionic sites on the resin which can bind with an acidic non-ionic lipid lowering agent and coated in an amount for taste-masking during chewing of a pharmaceutically acceptable acid resistant enteric phthalate soluble in intestinal juice of the proximal region of the small intestine, in which bile acids are present in significant amounts, and
   (b) acidic gemfibrozil or a pharmaceutically acceptable acidic derivative thereof.

2. A method of treating hypercholesteremia in a patient in need of such treatment comprising administering to that patient the composition of claim 1.

3. A candy formulation containing the composition of claim 1.

4. The composition of claim 1 wherein (a) contains cholestyramine, cholestipol or a pharmaceutically acceptable salt thereof.

5. The composition of claim 1 wherein (a) contains cholestyramine.

6. The composition of claim 1 wherein the pharmaceutically acceptable acid resistant material is cellulose acetate phthalate, or polyvinyl acetate phthalate.

* * * * *